(12) United States Patent
Machi

(10) Patent No.: US 10,905,448 B2
(45) Date of Patent: Feb. 2, 2021

(54) THROMBECTOMY DEVICE

(71) Applicant: Antonino Machi, Geneva (CH)

(72) Inventor: Antonino Machi, Geneva (CH)

(73) Assignee: Antonino Machi, Genève (CH)

(*) Notice: Subject to any disclaimer, the term of this patent is extended or adjusted under 35 U.S.C. 154(b) by 257 days.

(21) Appl. No.: 16/076,048

(22) PCT Filed: Feb. 9, 2017

(86) PCT No.: PCT/EP2017/052912
§ 371 (c)(1),
(2) Date: Aug. 7, 2018

(87) PCT Pub. No.: WO2017/137508
PCT Pub. Date: Aug. 17, 2017

(65) Prior Publication Data
US 2020/0129193 A1    Apr. 30, 2020

(30) Foreign Application Priority Data
Feb. 9, 2016 (FR) .................... 16 50998

(51) Int. Cl.
*A61B 17/22* (2006.01)
*A61B 17/221* (2006.01)
*A61B 17/00* (2006.01)
*A61M 25/01* (2006.01)

(52) U.S. Cl.
CPC .. *A61B 17/221* (2013.01); *A61B 2017/00867* (2013.01); *A61B 2017/22079* (2013.01); *A61M 25/0108* (2013.01)

(58) Field of Classification Search
CPC .......... A61B 17/221; A61B 17/320758; A61B 17/320725; A61B 17/320783; A61B 2017/00867; A61B 17/22; A61B 17/320016
See application file for complete search history.

(56) References Cited

U.S. PATENT DOCUMENTS

| | | | |
|---|---|---|---|
| 2012/0035649 A1 | 2/2012 | Kusleika | |
| 2014/0005712 A1* | 1/2014 | Martin | A61B 17/221 606/200 |
| 2014/0005717 A1 | 1/2014 | Martin et al. | |
| 2015/0025555 A1 | 1/2015 | Sos | |
| 2015/0223829 A1 | 8/2015 | Aboytes | |
| 2016/0000450 A1 | 1/2016 | Yu | |

OTHER PUBLICATIONS

International Search Report and Written Opinion dated May 30, 2017 for corresponding PCT Application No. PCT/EP2017/052912.

* cited by examiner

*Primary Examiner* — Vi X Nguyen
(74) *Attorney, Agent, or Firm* — Polsinelli PC

(57) ABSTRACT

The invention relates to a thrombectomy device (100), with a wire (105), referred to as a "push wire", attached to a woven structure (110) at the distal end of the woven structure, the woven structure surrounding, at the proximal end of the woven structure, an opening (115) having a diameter that varies on the basis of a configuration of the woven structure, and the woven structure having two configurations: an opened-out configuration in which the woven structure is radially spaced apart from the push wire so as to open the opening surrounded by the woven structure and is axially compressed toward the distal end, and a collapsed configuration in which the woven structure is radially near the push wire and axially extended along the push wire.

22 Claims, 3 Drawing Sheets

THROMBECTOMY DEVICE

CROSS-REFERENCE TO RELATED APPLICATIONS

This application is a national stage application (under 35 U.S.C. § 371) of PCT/EP2017/052912, filed Feb. 9, 2017, which claims benefit of French Application No. 1650998, filed Feb. 9, 2016, which are incorporated herein by reference in their entireties.

TECHNICAL FIELD OF THE INVENTION

The present invention relates to a thrombectomy device. It applies, in particular, to endovascular thrombectomy procedures.

STATE OF THE ART

An endovascular thrombectomy consists of the mechanical removal of a thrombus causing the occlusion of a patient's blood vessel, for example in the context of acute ischemic cerebral accidents (stroke). This type of procedure is currently done with thrombectomy devices that have, for example, a "stent" type cylindrical structure and a pusher that is attached to its proximal end, i.e., the end closest to the surgeon. Such systems are described, for example, in US patent application US 2014/0343595.

In current systems:
- a guide wire is inserted into the blood vessel of a patient with a vascular occlusion and positioned downstream of the thrombus,
- a microcatheter is then advanced along the guide wire beyond the thrombus,
- the guide wire is removed and the thrombectomy device is moved together with its pusher into the blood vessel through the microcatheter and deployed at the thrombus or just downstream of it,
- the thrombectomy device, still attached to the pusher by its proximal end, is removed so as to have an interaction with the thrombus, which occupies the vessel lumen.

The interaction between the thrombectomy device and the thrombus during removal allows the device to penetrate and capture the thrombus.

However, the removal of the device by its proximal end, especially in the presence of a rigid thrombus (for example, fibrin-rich or calcified) and/or tortuous vessels makes it that, when the device is removed, it follows the direction of force of the pusher and is flattened during contact with the thrombus without having any traction effect on it. Under these conditions, the thrombectomy device fails to remove the thrombus.

Furthermore, some known devices, once they are positioned against a thrombus and a traction force is applied to them, undergo an inversion sometimes called "socking". This inversion is caused by insufficient rigidity of the device which, confronted with the traction force, turns inside out, on the other side of a distal attachment end of the device to the pusher.

OBJECTIVE OF THE INVENTION

The present invention seeks to remedy all or part of these disadvantages. To this end, the present invention relates to a thrombectomy device that has:

- a wire, called "pusher" (push wire) attached to a braided structure at the distal end of the braided structure, the braided structure surrounding, at the proximal end of said braided structure, an opening (115) of variable diameter depending on a configuration of the braided structure and
- the braided structure having two configurations:
  - a deployed configuration, in which the braided structure is radially distant from the pusher to open the opening surrounded by the braided structure and compressed axially in the direction of the distal end and
  - a folded configuration, in which the braided structure is radially close to the pusher and extends axially along the pusher.

Via these arrangements, during the removal of the device, by exerting a traction force on the pusher, the braided structure takes on the form of the walls independently from the movement of the pusher and compresses axially, which gives it increased rigidity and the ability to collect the thrombus. This optimizes thrombus capture by preventing flattening of the braided structure. Thus, the device does not follow the direction of traction of the pusher but rather the direction of the blood vessel wall until entering into contact with the thrombus, this thrombus being removed from the wall and positioned inside the braided structure, which permits extracting it. The attachment of the braided structure to a distal end simultaneously induces movement along the axis of the vessel, and not the pusher, and the optimal deployment of the device.

In some embodiments, the device that is the subject of the present invention is associated with a suction catheter with a given diameter value into which the pusher is inserted, the braided structure having, in the deployed configuration, a diameter roughly equal to said diameter value.

These embodiments enable the thrombus to be captured by suction and, at the same time, by being held by a pincher movement between the braided structure deployed and compressed along the axial axis and the catheter. This prevents fragments of the thrombus from being released into the bloodstream during removal of the suction catheter and the thrombus.

In some embodiments, the braided structure has:
- a first part having a first diameter attached to the pusher and
- a second part, attached to the first part, having a second diameter greater than the first diameter.

These embodiments improve control of the deployment shape of the device when traction is exerted on the pusher attached to the device.

In some embodiments, the braided structure has, between the first and the second part, a third part of a third diameter comprised between the first and second diameter, this third diameter increasing from the first to the second part.

This third part, preferentially, has a braiding angle that allows it to expand by axial compression during removal. Moreover, the braiding angle, preferentially, keeps the device from inverting during removal.

These embodiments improve control of the deployment shape of the device when traction is exerted on the pusher attached to the device.

In some embodiments, the first and third part of the braided structure have a braiding angle comprised between 65 and 75 degrees.

The radial force of the device is related to the braiding angle: the greater the braiding angle, the greater the radial force.

In some embodiments, the first part has a length of ten millimeters and the third part has a length of five millimeters.

In some embodiments, the braided structure has a fourth part attached to one end of the second part, this fourth part having a fourth diameter less than the second diameter, this fourth diameter decreasing from the second part.

This fourth part, folded toward the lumen of the device, allows the device to have nontraumatic interaction during removal with the arterial angles, which are found, for example, at arterial bifurcations.

These embodiments help to improve the expansion of the device during traction.

In some embodiments, the fourth part has a braiding angle comprised between 45 and 55 degrees.

The fourth part must have a lower radial force relative to the other parts because it must be able to be inverted a little, notably to better capture the thrombus and at the same time to be nontraumatic for the vessel walls; this behavior is in particular due to the braiding angle.

In some embodiments, the fourth part has a diameter, in deployed configuration, of 1.5 millimeters.

In some embodiments, the second part of the braided structure has a braiding angle comprised between 65 and 75 degrees.

In some embodiments, the second part has a length of six millimeters.

In some embodiments, the second part has, over four millimeters, from the attachment to the first part, a braiding angle comprised between 65 and 75 degrees.

In some embodiments, the second part has, over two millimeters, from four millimeters from the attachment to the first part, a braiding angle comprised between 45 and 55 degrees.

The braiding angle of the various segments combined with their length keeps the device from being flattened and from inverting in response to the thrombus during removal.

In some embodiments, the second part has a diameter, in deployed configuration, of two millimeters.

The dimensioning of the lengths and braiding angles of these particular embodiments all participate in reducing the inversion effect of the device when traction is exerted on the pusher.

In some embodiments, the braided structure is made of an elastic material with shape memory.

Thus, once the device is positioned inside the blood vessel, the braided structure takes the deployed configuration spontaneously.

In some embodiments, at least a part of the braided structure is covered by a platinum coating.

These embodiments have the advantage of making the device radiopaque.

In some embodiments, the pusher has a distal attachment point to the braided structure, this braided structure having wires sliding over one another so as to form meshes of variable dimensions depending on the opening status of the braided structure.

These embodiments allow the wires to slide to go from one configuration to the other.

In some particular embodiments, the braided structure is formed from between 4 and 400 braided wires.

In some particular embodiments, the braided structure is formed from between 10 and 100 braided wires.

In some particular embodiments, the braided structure is formed from between 20 and 50 braided wires.

Preferentially, 36 wires are used to form said structure.

In some particular embodiments, each wire of the structure has a diameter comprised between 1 and 100 micrometers.

In some particular embodiments, each wire of the structure has a diameter comprised between 10 and 80 micrometers.

In some particular embodiments, each wire of the structure has a diameter comprised between 15 and 50 micrometers.

Preferentially, the wire diameter is equal to 30 micrometers.

BRIEF DESCRIPTION OF THE FIGURES

Other particular advantages, objectives and characteristics of the invention will appear from the non-limiting description that follows of at least one particular embodiment of the device and the method that are the subject of the present invention with regard to the attached drawings, in which.

DESCRIPTION OF EXAMPLES OF EMBODIMENT OF THE INVENTION

The present description is given by way of non-limiting example; each characteristic of an embodiment can be combined with any other characteristic of any other embodiment advantageously.

Figure 1:
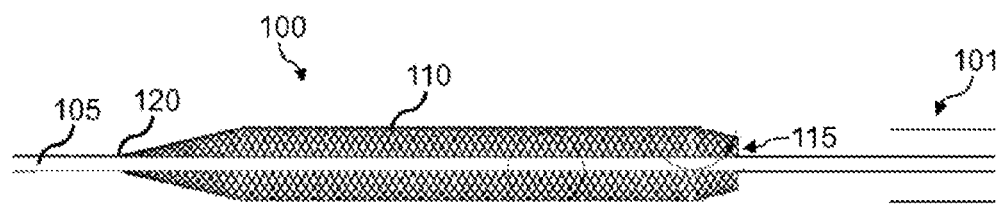
FIG. 1 shows, schematically and in section, one particular embodiment of the device that is the subject of the present invention.
Figure 2:
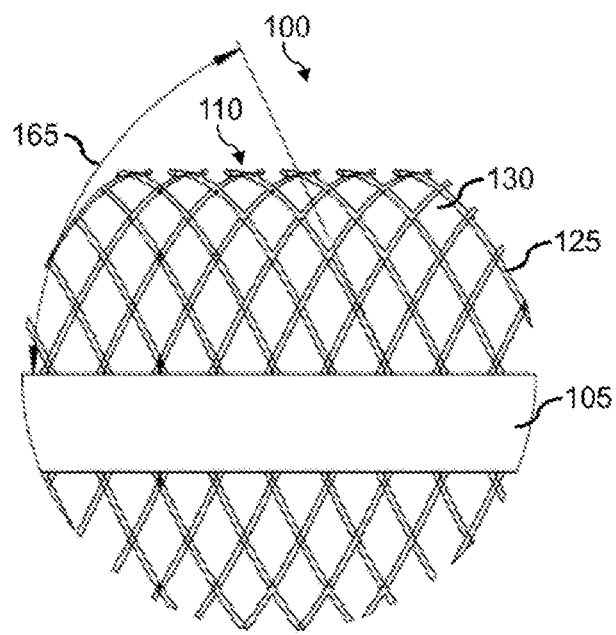
FIG. 2 shows, schematically and in section, one particular embodiment of the device that is the subject of the present invention.
Figure 3:
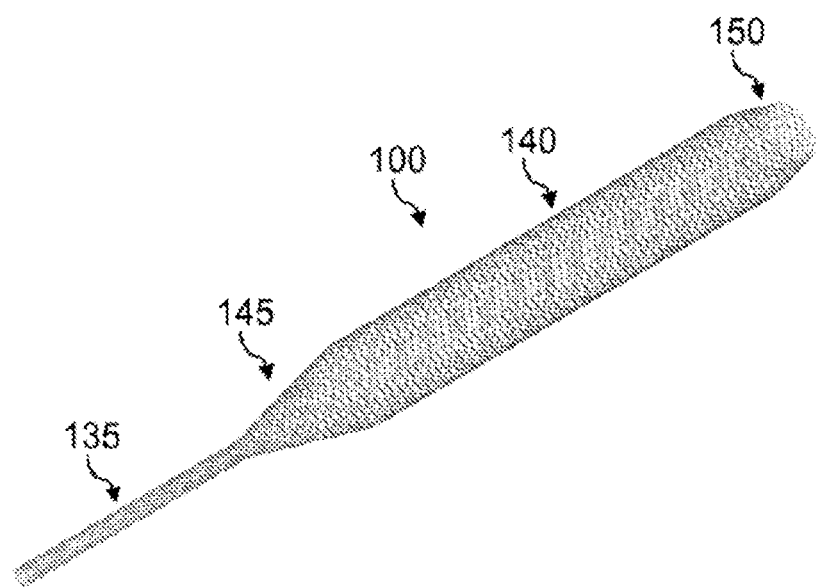
FIG. 3 shows, schematically and in perspective, one particular embodiment of the device that is the subject of the present invention.
Figure 4:
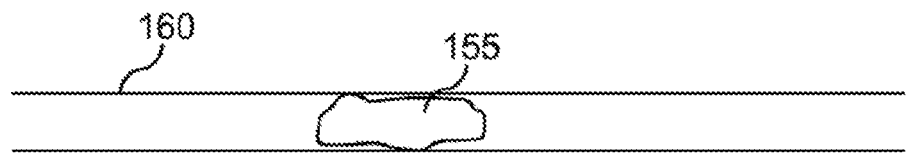
FIGS. 4 to 7 show, schematically and in section, one particular application of the particular embodiment of the device that is the subject of the present invention
Figure 5:
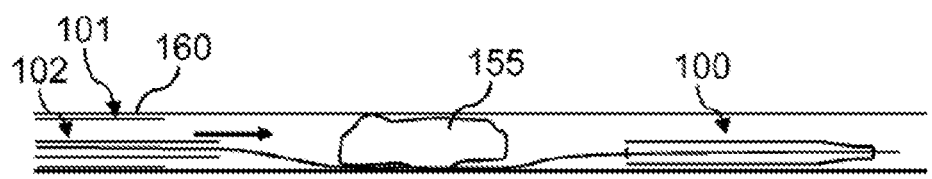
Figure 6:
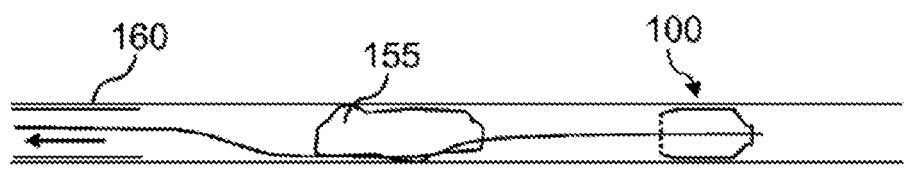
Figure 7:
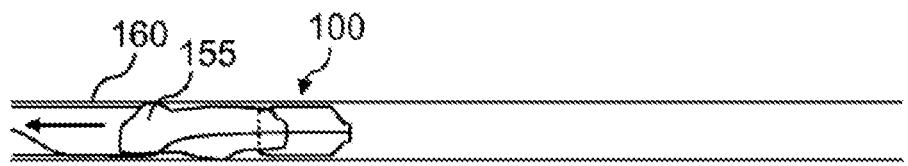

In FIGS. 1 to 3, which are not to scale, a schematic view of one embodiment of the device 100 that is the subject of the present invention is observed. This thrombectomy device 100 has:

a wire 105, called "pusher" attached to a braided structure 110 at the distal end of the braided structure, the braided structure 110 surrounding, at the proximal end of said braided structure 110, an opening 115 of variable diameter depending on a configuration of the braided structure 110 and the braided structure 110 having two configurations:
a deployed configuration, in which the braided structure is radially distant from the pusher to open the opening surrounded by the braided structure and, when traction is exerted on the pusher, compressed axially in the direction of the distal end and
a folded configuration, in which the braided structure is radially close to the pusher and extends axially along the pusher, in the absence of traction on said pusher.

The pusher 105 is, for example, a stainless-steel wire with a diameter of around 0.35 millimeters and a length of around two meters. Preferentially, this wire is made radiopaque by the addition of a platinum coating.

This pusher 105 is attached, near the distal end of the braided structure 110.

This braided structure 110 is formed of braided wires with a diameter of 30 or 32 micrometers, for example. This structure is formed of 4 to 400 wires, and preferentially 36. This braided structure 110 permits the wires to slide over one another, which allows optimal radial expansion and axial compression of the braided structure 110 when the device 100 is removed from the blood vessel.

The wires forming the braided structure 110 have a certain elasticity and are preferentially made of an elastic material with shape memory such as, for example, a titanium and nickel alloy called "nitinol" or chromium and cobalt. Thus, as soon as device 100 is positioned in a blood vessel, the braided structure 110 extends to come into contact with the blood vessel walls.

This braided structure 110 has two ends:
- one is called "distal"; this end is attached near the distal end of the pusher 105 and
- the other is called "proximal"; this end is further from the distal end of the pusher 105 than the distal end of the braided structure 110.

In this way, the distal end of the braided structure 110 is positioned downstream of the proximal end of the braided structure 110 relative to the thrombus when the braided structure 110 is integrally located downstream of the thrombus relative to the blood flowing through the blood vessel.

The braided structure 110 surrounds, at the proximal end of the braided structure 110, an opening 115 intended to allow the passage of the thrombus when the braided structure 110 is in the deployed configuration during the removal of the device 100.

Therefore, as can be understood, exerting a traction force on the pusher, i.e., a force seeking to move the pusher 105 towards an opening created in the blood vessel, induces the deployment of the braided structure 110 and an axial compression.

During this removal, the braided structure 110 undergoes radial expansion and consequently axial compression.

This braided structure 110 has, for example, a length of twenty-five millimeters in folded configuration, i.e., at rest. This braided structure 110 has, for example, a diameter of two millimeters in deployed configuration.

The "braiding angle" is the angle between:
- the projection from one point of a wire of the braided structure 110 on a plane perpendicular to the radius of the braided structure 110 passing through this point and through the central axis of symmetry of the braided structure 110 and
- the central axis of the braided structure 110.

The braided structure 110 is attached to the pusher 105, for example, by soldering, gluing or crimping or with a mechanical tool.

Preferentially, the pusher 105 has a distal attachment point 120 to the braided structure 110, this braided structure having wires 125 sliding over one another so as to form meshes 130 of variable dimensions depending on the opening status of the braided structure.

The dimensions of these meshes are smaller when the device 100 is in deployed configuration.

Preferentially, the pusher 105 and braided structure 110 are introduced into the blood vessel by the use of a microcatheter 102. This microcatheter 102 has, for example, a diameter of less than two millimeters.

Preferentially, the braided structure 110 has:
- a first part 135 having a first diameter attached to the pusher 105 and
- a second part 140, attached to the first part, 135 having a second diameter greater than the first diameter.

The first diameter is, for example, constant along the device 100 and attached along the entire length of the pusher 105 so as to reinforce the attachment.

This first diameter is, for example, equal to 0.35 millimeters.

The first part 135 has, for example, a length of one centimeter.

The second part 140 has a second diameter, variable depending on the configuration of the braided structure 110. In any case, this second diameter is greater than or equal to the first diameter regardless of the configuration the braided structure 110 is in.

The second part 140 has, for example, a length of 6 millimeters.

Preferentially, the braided structure 110 has, between the first and the second part, 135 and 140, a third part 145 of a third diameter comprised between the first and second diameter, this third diameter increasing from the first 135 to the second part 140.

The third part 145 has, for example, a length of five millimeters. This third part 145 has, at the area of contact with the first part 135, a diameter equal to the diameter of the first part 135 and, at the area of contact with the second part 140, a diameter equal to the diameter of the second part 140.

Preferentially, the first and third part, 135 and 145, of the braided structure have a braiding angle comprised between 65 and 75 degrees. Preferentially, this angle is equal to 70 degrees.

Preferentially, the first part 135 has a length of ten millimeters and the third part 145 of the has a length of five millimeters.

Preferentially, the second part 140 of the braided structure has a braiding angle comprised between 65 and 75 degrees. Preferentially, this angle is equal to 70 degrees.

Preferentially, the second part 140 has a length of six millimeters.

Preferentially, the second part 140 has, over four millimeters, from the attachment to the first part 135, a braiding angle comprised between 65 and 75 degrees. Preferentially, this angle is equal to 70 degrees.

Preferentially, the second part 140 has, over two millimeters, from four millimeters from the attachment to the first part 135, a braiding angle comprised between 45 and 55 degrees. Preferentially, this angle is equal to 50 degrees.

Preferentially, the second part 140 has a diameter, in deployed configuration, of two millimeters.

This dimensioning allows the device to have a radial and structural force preventing any inversion.

Preferentially, the braided structure 110 has a fourth part 150 attached to one end of the second part 140, this fourth part 150 having a fourth diameter less than the second diameter, this fourth diameter decreasing from the second part 140.

The fourth part 150 has, for example, a length of four millimeters.

Preferentially, the fourth part 150 has a braiding angle comprised between 45 and 55 degrees. Preferentially, this braiding angle is equal to 50 degrees.

Preferentially, the fourth part 150 has a diameter, in deployed configuration, of 1.5 millimeters.

This dimensioning allows the device to have, at the end formed by the fourth part, a reduced rigidity to limit the risks of catching on the walls of the blood vessel.

In some embodiments, the device 100 is associated with a suction catheter 101 with a given diameter value in which the pusher is inserted, the braided structure having, in the deployed configuration, a diameter roughly equal to said diameter value.

In FIGS. 4 to 7, successively, the different steps are observed of the removal of a thrombus by the device 100 that is the subject of the present invention. In particular, the following is observed:
- in FIG. 4, a blood vessel 160 obstructed by a thrombus 155,
- in FIG. 5, the device 100 inserted into the blood vessel 160 upstream of the thrombus 155, relative to the blood flow, and passing the thrombus 155 so as to be positioned downstream of said thrombus 155,
- in FIG. 6, the braided structure deployed and compressed along the axial plane by a traction movement exerted on the wire and the device 100 along a different direction of movement relative to the pusher 105,
- in FIG. 7, the thrombus 155 captured by the braided structure 115, this thrombus can be freely extracted from the blood vessel 160 by removal of the device 100 or moved closer to the suction catheter.

Figure 8:
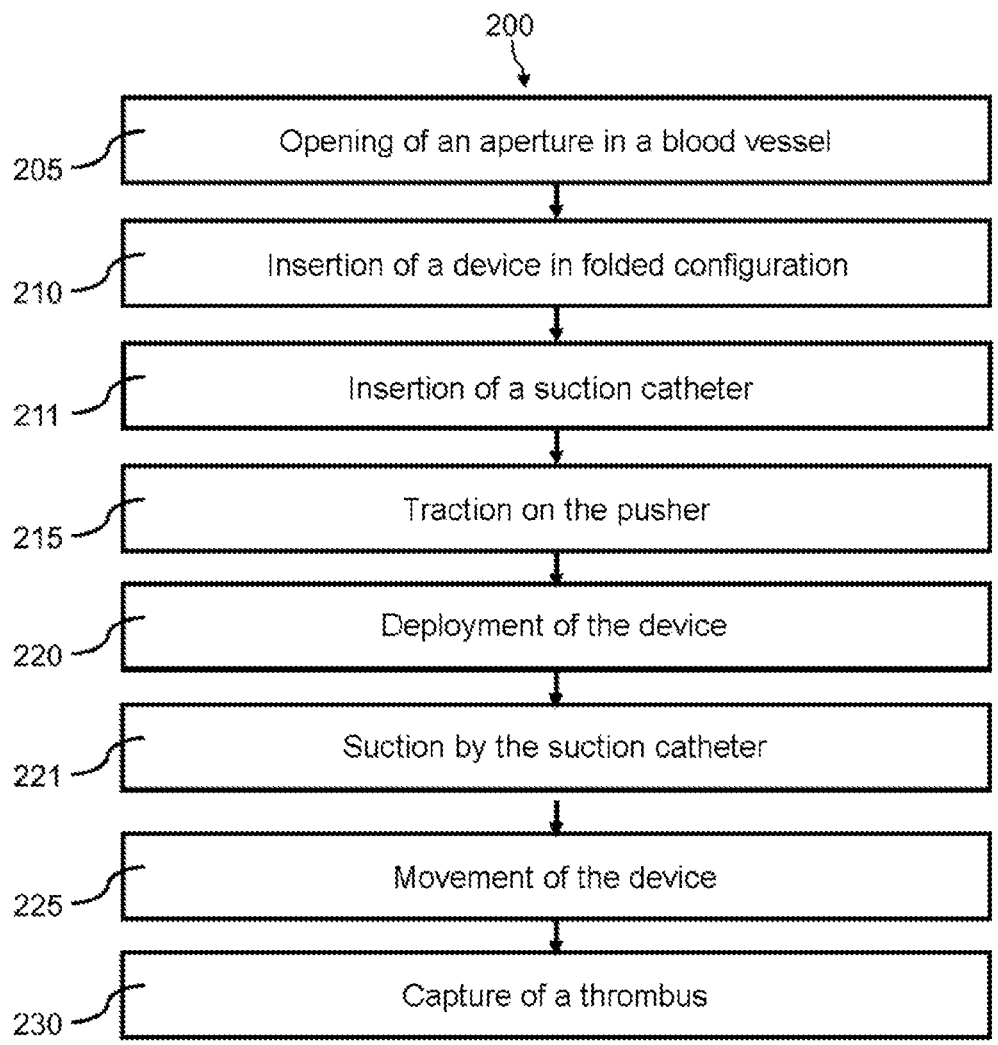
FIG. 8 shows, schematically and in the form of a flow chart, a particular succession of steps of the method that is the subject of the present invention.

In FIG. 8, a particular method embodiment 200 corresponding to the steps illustrated in FIGS. 4 to 7 is observed schematically. This thrombectomy method 200 has:
- a step 205 of opening of a lumen in a blood vessel upstream of the thrombus to be operated on relative to the blood flowing in the blood vessel,
- a step 210 of inserting a device 100, such as described in regard to FIGS. 1 to 3, into the blood vessel, by means of a microcatheter 102, for example, the braided structure of this device 100 being in folded configuration,
- a step of extracting the device 100 from the microcatheter 102 so that the device can be positioned downstream of the thrombus and so that the braided structure 110 is deployed by shape memory,
- optionally, a step 211 of inserting a suction catheter 101 surrounding the microcatheter, this step being able to be done before or after insertion step 210,
- a step 215 of traction on the wire to induce optimal deployment 220 and simultaneous movement 225 of the device 100 along the blood vessel walls, regardless of the traction exerted on the pusher,
- optionally, a suction step 221 conducted by suction catheter 101, this suction step 221 being able to be done before or after traction step 215 and
- a step 230 of capturing the device in the opening surrounded by the braided structure.

The invention claimed is:

1. A thrombectomy device (100) comprising:
a wire (105), called "pusher" attached to a braided structure (110) at the distal end of the braided structure, the braided structure surrounding, at the proximal end of said braided structure, an opening (115) of variable diameter depending on a configuration of the braided structure and
the braided structure having two configurations:
 a deployed configuration, in which the braided structure is radially distant from the pusher to open the opening surrounded by the braided structure and compressed axially in the direction of the distal end, and
 a folded configuration, in which the braided structure is radially close to the pusher and extends axially along the pusher,
 wherein the braided structure passes from the folded configuration to the deployed configuration when a traction force is exerted on the pusher, and
wherein the braided structure (110) has:
 a first part (135) having a first diameter attached to the pusher (105), and
 a second part (140), attached to the first part, having a second diameter greater than the first diameter, the second part (140) being proximally located with respect to the first part (135).

2. The device (100) as claimed in claim 1, which is associated with a suction catheter (101) with a given diameter value into which the pusher is inserted, the braided structure having, in the deployed configuration, a diameter roughly equal to said diameter value.

3. The device (100) as claimed in claim 1, in which the braided structure has, between the first and the second part (135, 140), a third part (145) of a third diameter comprised between the first and second diameter, this third diameter increasing from the first to the second part.

4. The device (100) as claimed in claim 3, in which the first and third part (135, 145) of the braided structure have a braiding angle comprised between 65 and 75 degrees.

5. The device (100) as claimed in claim 3, in which the first part (135) has a length of ten millimeters and the third part (145) of the has a length of five millimeters.

6. The device (100) as claimed in claim 1, in which the braided structure has a fourth part (150) attached to one end of the second part (140), this fourth part having a fourth diameter less than the second diameter, this fourth diameter decreasing from the second part.

7. The device (100) as claimed in claim 6, in which the fourth part (150) has a braiding angle comprised between 45 and 55 degrees.

8. The device (100) as claimed in claim 6, in which the fourth part (150) has a diameter, in deployed configuration, of 1.5 millimeters.

9. The device (100) as claimed in claim 1, in which the second part (140) of the braided structure has a braiding angle comprised between 65 and 75 degrees.

10. The device (100) as claimed in claim 9, in which the second part (140) has, over four millimeters, from the attachment to the first part (135), a braiding angle comprised between 65 and 75 degrees.

11. The device (100) as claimed in claim 10, in which the second part (140) has, over two millimeters, from four millimeters from the attachment to the first part (135), a braiding angle comprised between 45 and 55 degrees.

12. The device (100) as claimed in claim 1, in which the second part (140) has a length of six millimeters.

13. The device (100) as claimed in claim 1, in which the second part (140) has a diameter, in deployed configuration, of two millimeters.

14. The device (100) as claimed in claim 1, in which the braided structure is made of an elastic material with shape memory.

15. The device (100) as claimed in claim 1, in which at least a part of the braided structure (110) is covered by a platinum coating.

16. The device (100) as claimed in claim 1, in which the pusher has a distal attachment point (120) to the braided structure (110), this braided structure having wires (125) sliding over one another so as to form meshes (130) of variable dimensions depending on the opening status of the braided structure.

17. The device (100) as claimed in claim 1, in which the braided structure is formed from between 4 and 400 braided wires.

18. The device (100) as claimed in claim 1, in which each wire of the structure has a diameter comprised between 1 and 100 micrometers.

19. A method for removing a thrombus from a blood vessel of a patient in need thereof, comprising:
  a) inserting the device of claim 1 into the blood vessel upstream of the thrombus, relative to the blood flow, and passing the thrombus so as to position the device downstream of the thrombus, wherein the braided structure is in the folded configuration,
  b) exerting traction on the pusher to induce deployment of the braided structure, and
  c) capturing the thrombus by deploying the braided structure.

20. The method of claim 19, wherein the thrombus is extracted from the blood vessel by removal of the device.

21. The method of claim 19, wherein the thrombus is extracted from the blood vessel by suction with a suction catheter introduced in the blood vessel between a) and b).

22. The device (100) as claimed in claim 1, wherein the braided structure (110) is radially close to the pusher and extends axially along the pusher in the absence of traction on the pusher.

\* \* \* \* \*